(12) United States Patent
Murauski

(10) Patent No.: US 8,632,986 B2
(45) Date of Patent: Jan. 21, 2014

(54) METHODS AND KITS FOR DETECTION OF TOXEMIA

(76) Inventor: Uladzimir A. Murauski, Wildau (DE)

( * ) Notice: Subject to any disclaimer, the term of this patent is extended or adjusted under 35 U.S.C. 154(b) by 202 days.

(21) Appl. No.: 13/126,624

(22) PCT Filed: Nov. 21, 2008

(86) PCT No.: PCT/EP2008/066030
§ 371 (c)(1),
(2), (4) Date: Jul. 11, 2011

(87) PCT Pub. No.: WO2010/049010
PCT Pub. Date: May 6, 2010

(65) Prior Publication Data
US 2011/0269245 A1  Nov. 3, 2011

Related U.S. Application Data

(60) Provisional application No. 61/109,008, filed on Oct. 28, 2008.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

U.S. PATENT DOCUMENTS

| | | | |
|---|---|---|---|
| 5,183,740 A | 2/1993 | Ligler et al. | |
| 5,308,604 A | 5/1994 | Sinn et al. | |
| 6,306,576 B1 | 10/2001 | Mazen et al. | |
| 6,458,758 B1 | 10/2002 | Hsia | |
| 6,589,751 B2 | 7/2003 | Ferguson et al. | |
| 6,989,369 B2 | 1/2006 | Ladner et al. | |
| 7,060,292 B2 | 6/2006 | Melchior et al. | |
| 7,070,937 B1 | 7/2006 | Bar-Or et al. | |
| 7,166,474 B2 | 1/2007 | Muravsky et al. | |
| 7,172,873 B2 | 2/2007 | McDonald et al. | |
| 7,238,667 B2 | 7/2007 | Rosen et al. | |
| 2003/0143191 A1 | 7/2003 | Bell et al. | |
| 2003/0170912 A1 | 9/2003 | Muravsky et al. | |
| 2006/0122374 A1 | 6/2006 | Mertins et al. | |
| 2007/0231847 A1 | 10/2007 | Bar-Or et al. | |
| 2007/0275483 A1 | 11/2007 | Liotta et al. | |

FOREIGN PATENT DOCUMENTS

| | | |
|---|---|---|
| EP | 0973043 | 1/2000 |
| SU | 1459656 | 2/1989 |
| WO | 9420863 | 9/1994 |
| WO | 2007041596 | 4/2007 |
| WO | 2007079886 | 7/2007 |
| WO | 2010/049010 A1 | 5/2010 |

OTHER PUBLICATIONS

Altamentova et al. Clinica Chimica Acta, vol. 271, No. 2, Mar. 23, 1998, pp. 133-149.*
International Search Report and Written Opinion issued in PCT/EP2013/053389, mailed Jun. 13, 2013.
Gelos et al., "Analysis of albumin fatty acid binding capacity in patients with benign and malignant colorectal diseases using electron spin resonance (ESR) spectroscopy", International Journal of colorectal Disease, 25(1): 119-127, 2009.
Altamentova et al. A fluorescence method for estimation of toxemia: Binding capacity of lipoproteins and albumin in plasma. Clinica Chimca Acta. 271(2). 133-149. 1998.
Caldararu et al. A spin probe study of mesoporous silica formation via a neutral templating route. Journal of Physical Chemistry Part B: Condensed Matter, Materials, Surfaces, Interfaces & Biophysical. 107(25):6032-6038. 2003.
Gurachevsky et al. Application of spin label electron paramagnetic resonance in the diagnosis and prognosis of cancer and sepsis. Clin. Chem. Lab Med. 2008. vol. 46. No. 9. pp. 1203-1210. 2008.
Office Communication. Issued in European Application No. 08 875 351.2. Mailed on Mar. 30, 2012.
PCT International Preliminary Report on Patentability issued in International application No. PCT/EP2008/066030. Dated May 3, 2011.
PCT International Search Report issued in International application No. PCT/EP2008/066030. Dated Jul. 3, 2009.
Smirnova. Binding of MRI contrast agents to albumin: A high-field EPR study. Applied Magnetic Resonance. 31 (3-4). 431-446. 2007.
Office Communication. Issued in European Application No. 08 875 351.2. Dated Feb. 4, 2013.

* cited by examiner

*Primary Examiner* — Lisa Cook
(74) *Attorney, Agent, or Firm* — Dowell & Dowell, PC

(57) ABSTRACT

Various embodiments of methods and kits are disclosed for prognosis, detection, and/or diagnosis of toxemia in a subject patient by analyzing an aliquot of the subject patient's extracellular fluid (e.g., blood serum) that contains carrier proteins.

26 Claims, 5 Drawing Sheets a) 16-DOXYL-stearic acid, free radical b) 5-DOXYL-stearic acid, free radical c) 16:0-16 PC DOXYL, free radical (1-Palmitoyl-2-Stearoyl-(16-DOXYL)-sn-Glycero-3-Phosphocholine)

d) 18:0 PC C13 (1,2-Distearoyl[1-13C]-sn-Glycero-3-Phosphocholine), Carbon-13 labeled e) Oleic acid-1,2,3,7,8,9,10-13C7, Carbon-13-labeled f) 12-N-Methyl-7-nitrobenzo-2-oxa-1,3-diazolamino stearate [12-NBDS or NBD-stearate], fluorescent probe (Fluorescent labeled stearic acid). CAS Registry: 117056-67-4 g) 12-(9-anthroyl)stearic acid [ anthroylstearic acid ], fluorescent probe (Fluorescent labeled stearic acid). CAS Registry: 37469-99-1

METHODS AND KITS FOR DETECTION OF TOXEMIA

CROSS REFERENCE TO RELATED APPLICATIONS

This parent application is a National Phase application claiming the benefit of PCT/EP2008/066030 filed on Nov. 21, 2008; which further claims priority to U.S. Provisional Application No. 61/109,008 filed on Oct. 28, 2008, the entire contents of which are incorporated herein by reference.

BACKGROUND OF THE INVENTION

1. Field of the Invention

The present invention relates generally to analysis of extracellular fluids that contain carrier proteins, and, more particularly, but not by way of limitation, to methods for prognosis and detection of toxemia in a patient by analyzing a serum sample from the patient.

2. Description of Related Art

For illustration, but without limiting the scope of the invention, the background is described with respect to analyzing the blood of a human patient.

In the early stages of toxemia, the ability of a patient's body to evacuate toxins from the blood stream may become compromised. That is, the patient's biological systems for evacuating toxins from the patient's blood stream may stop functioning properly and begin to permit toxins to build in the patient's body. In later stages of toxemia, these toxins generally reach relatively high levels (as compared to normal, toxin levels in a healthy patient), and the toxins may begin to cause noticeable symptoms such as illness, cell damage, organ failure, and the like. Currently known methods of diagnosing toxemia may not permit recognition or diagnosis of toxemia until later stages when symptoms are already noticeable. In these later stages, treatment may be less effective and may not be effective enough to prevent the death of the patient.

Analyzing hematologic parameters and/or measuring the concentration of various metabolites in blood samples from a patient are known in the art and may be widely-used methods of diagnosing toxemia (which may also be known in the art as toxaemia) in a patient, such as, for example, in a clinical setting. However, these known methods suffer a number of shortcomings and/or drawbacks.

One example of a known method may be referred to in the art as the "mean mass molecules" evaluation of a sample of a patient's blood serum. However, in the "mean mass molecules" evaluation, generally only a fraction of unbound, free endogenous toxins in the serum may be detected. This fraction may also be limited in that it may contain mostly toxins that are hydrophilic. "Absorbed" or "bound" hydrophobic toxins, which are respectively adsorbed on biological membranes or bound on carrier proteins, may not be detected. The failure to detect absorbed hydrophobic toxins can be detrimental to the treatment and recovery of the patient because these toxins may subsequently damage, or may have already damaged, cells, organs or systems in the patient. Such damage, caused by these absorbed and/or bound hydrophobic toxins, may subsequently cause changes in hematological parameters and/or other symptoms of toxemia.

Because the "mean mass molecules" evaluation (as well as other known methods of detecting toxemia) may not detect hydrophobic toxins, toxemia may not be detected until cells have been significantly damaged and/or hematologic changes or failures have already occurred. Stated otherwise, known methods of detecting toxemia may not detect toxemia in its early stages, and instead, may only detect toxemia in later stages of its development when it may be substantially harder to treat it effectively. In these later stages of toxemia, treatment may be inhibited by factors such as, for example, reduced capacity of the carrier proteins to evacuate toxins, and/or reduced capacity of the patients liver to detoxify or remove the toxins from the carrier proteins.

Soviet Union Patent, SU 1,459,656, published Feb. 23, 1989, describes a method of diagnosing endogenous toxemia by an evaluation of the ability of erythrocyte membranes to bind the fluorescent probe ANS. This method may permit detection of damage to erythrocyte membranes that has already occurred due to erythrocyte interaction with toxins (either hydrophilic or hydrophobic). This method may permit relatively-earlier detection of toxemia in a patient, such as, for example, at a stage in which toxins have already damaged cell membranes but before the damage is extensive enough to cause failure of organs and/or systems of the patient. Practically speaking, this method may permit detection of toxemia as much as approximately 6 to 12 hours before other hematological parameters show detectible changes or before other symptoms may appear. This method therefore still suffers from the shortcoming that it may not detect toxemia before toxins have damaged cells of the patient, and therefore may not permit treatment early enough during the development of the disease to prevent or minimize the effects, complications, or symptoms of toxemia.

U.S. Pat. No. 7,166,474 describes a method of detecting changes in transport properties of albumin by using electron paramagnetic resonance (EPR) spectroscopy (which may also be known in the art as electron spin resonance "ESR" spectroscopy) to evaluate a sample that contains albumin (an albumin-containing sample). This method can include evaluating the albumin transport function with respect to long chain fatty acids by using a spin probe represented by a spin-labeled fatty acid. Specifically, according to this method, the EPR-spectra of the spin probe can be measured in at least three aliquots of the sample, where each aliquot is mixed with significantly different concentrations of the spin probe and a high concentration of ethanol. The concentration of ethanol is high enough to induce significant conformational changes of the albumin to enable evaluation of the conformational flexibility of the albumin. The parameters of albumin transport function are derived from measurements of the conformational changes induced in the albumin artificially by the high ethanol concentration. This method assumes that albumin molecules efficiently release bound substances to target objects at conditions that occur in a healthy patient, and therefore induces a conformational change facilitating dissociation of albumin-bound ligands. While this may be useful in the method taught by this patent, the conformational changes induced by the high ethanol concentration prevents evaluation of the toxin-scavenging (toxin-binding) function of the albumin, because it assumes delivery of albumin-bound toxins to an excretion system, e.g. liver, rather than distribution of toxins throughout an organism in way similar to the delivery of nutrients to cells (permitting toxins to damage cells), as can happen in toxemic patients. This method suffers from possible shortcomings that may include, for example, the use of at least three aliquots of each sample, the fact that evaluation may be limited to certain albumin parameters, and excessive dissociation of bound substances (e.g., toxins) from the albumin (and/or from other serum proteins) resulting from the addition of relatively high-concentrations of ethanol. These possible shortcomings may contribute to variations in results and false-negatives in detecting the presence of protein-bound toxins in patients' blood.

A continuing need therefore exists for improved, faster, less-expensive, and/or more-accurate methods of detecting toxemia, especially in its early or precursor stages.

SUMMARY OF THE INVENTION

Various embodiments of the present invention can be suitable for detecting variations in carrier-protein functions, characteristics, and/or parameters by mixing various substances with a sample of extracellular fluid (that contains carrier proteins) from a subject patients, and analyzing the mixture. Examples of such extracellular fluids include blood serum, lymph fluid, and spinal fluid. Some embodiments of the present methods are suitable for prognosis (predicting the onset of), detection, or diagnosis of toxemia in its early or precursor stages. The present invention may be suitable, for example, for diagnosis and/or monitoring of toxemia in patients in clinical settings such as intensive care units. By way of further examples, the present invention may be suitable for such diagnosis, prognosis, or monitoring of patients in post-surgery recovery, or patients with or suffering from trauma, infection, sepsis, systemic inflammatory response syndrome (SIRS), stroke or brain attack, infarction, or the like.

In some embodiments, the methods of the present invention can be suitable for detection, diagnosis, or prognosis of toxemia, by detecting or measuring the deviation of the binding efficiency of carrier proteins of a subject patient, relative to the binding efficiency of carrier proteins of a control patient. The binding efficiency of carrier proteins of the control patient can be established, for example, by testing one or more control patients, by historical test results from patients with known conditions, by statistical aggregation of data from various other patients, or by any other suitable means that permits comparison with the subject patient in such a way as to provide an indication of whether the subject patient has, likely has, is likely to have, does not have, likely does not have, or is not likely to have toxemia. This deviation can, for example, be detected or measured for a sample of serum taken from a subject patient by mixing an aliquot of the serum sample with a labeled hydrophobic probe having a long-hydrocarbon-chain. Specifically, parameters of binding efficiency of a hydrophobic probe having a long-hydrocarbon chain to serum carrier proteins can correlate to the amount of toxic substances bound to the binding sites of the carrier proteins. This correlation can, for example, be caused by competitive binding on specific protein sites for substances with long hydrocarbon chains, and indirectly due to allosteric modification of the affinity of these sites upon ligand binding on other protein sites. Stated otherwise, when high levels of toxins are present in the subject patient's blood, the toxins may crowd and/or modify the binding sites of the carrier proteins, thereby preventing the hydrophobic probe from binding to those binding sites. In this way, hydrophobic toxins can be detected as their levels rise, and even before they damage cells.

The present invention includes various embodiments of methods for detecting toxemia in a subject patient. Some embodiments of the present method can comprise obtaining an aliquot from a sample of a subject patient's extracellular fluid containing carrier proteins. Some embodiments of the present methods can comprise mixing a labeled hydrophobic probe with the aliquot. In some of these embodiments, the amount of probe can be such that the molar ratio of probe capable of binding to (with) carrier proteins to the carrier proteins is between about 0.3 and about 1.5. Some embodiments of the present methods can comprise mixing a solvent into the aliquot. In some of these embodiments, the solvent can be such that when added to the aliquot and probe the solubility of the probe is increased in the aliquot. In some of these embodiments, the amount of solvent mixed with the aliquot can be sufficient to dissociate a portion of the probe from the carrier proteins without causing significant dissociation of toxins from the carrier proteins. In some embodiments, the amount of solvent mixed with the aliquot can be described as sufficient to dissociate a portion of the probe from the carrier proteins without causing dissociation of toxins from the carrier proteins.

Some embodiments of the present methods comprise analyzing the mixture of the aliquot, probe, and solvent to determine the binding efficiency of the carrier proteins. Some of these embodiments can comprise comparing the subject binding efficiency to at least one control binding efficiency for at least one non-toxemic control patient.

Some embodiments of the present methods can comprise analyzing the mixture of aliquot, probe, and solvent to determine a subject toxin-evacuation parameter of the carrier. Some of these embodiments can comprise comparing the subject toxin-evacuation parameter to at least one control toxin-evacuation parameter for a non-toxemic control patient. In some of these embodiments, analyzing the mixture can comprise measuring the concentrations of protein-bound and unbound probe in the mixture; deriving a subject binding efficiency of the carrier proteins from at least the concentrations of the protein-bound and unbound probe; and deriving a subject toxin-evacuation parameter of the carrier proteins as the square of the subject binding efficiency.

The present invention includes various embodiments of kits for detecting toxemia in a subject patient from a sample of the subject patient's extracellular fluid containing carrier proteins. Some embodiments of the present kits can comprise a labeled hydrophobic probe. In some of these embodiments, the amount of probe can be such that when mixed with an aliquot having a predetermined volume of the extracellular fluid the molar ratio of probe capable of binding with (to) carrier proteins to the carrier proteins is between about 0.3 and about 1.5. Some embodiments of the present kits can comprise a solvent. In some of these embodiments, the solvent can be such that when mixed with the probe and the aliquot the solubility of the probe is increased in the aliquot. In some of these embodiments, the amount of solvent can be sufficient to dissociate a portion of the probe from the carrier proteins without causing significant dissociation of toxins from the carrier proteins. In some embodiments, the amount of solvent can be described as sufficient to dissociate a portion of the probe from the carrier proteins without causing dissociation of toxins from the carrier proteins.

Some embodiments of the present kits can comprise instructions for performing the various embodiments of the present methods using one or more elements of the present kits. For example, some embodiments of the present kits can comprise instructions for: obtaining an aliquot having a predetermined volume of a sample of the subject patient's extracellular fluid containing carrier proteins; mixing a labeled hydrophobic probe with the aliquot, the amount of probe such that the molar ratio of probe capable of binding with (to) carrier proteins to the carrier proteins is between about 0.3 and about 1.5; mixing a solvent with the aliquot sufficient to dissociate a portion of the probe from the carrier proteins without causing significant dissociation of toxins from the carrier proteins; analyzing the mixture of the aliquot, probe, and solvent to determine the binding efficiency of the carrier proteins; comparing the subject binding efficiency to at least one control binding efficiency for a non-toxemic control patient; measuring the concentrations of protein-bound and unbound probe in the mixture; deriving a subject binding efficiency of the carrier proteins from at least the concentrations of the protein-bound and unbound probe; and/or any other steps or limitations described herein.

In some embodiments of the present methods, the probe and the solvent can be mixed with one another prior to either being mixed with the aliquot.

In some embodiments of the present methods and kits, the probe can comprise an organic molecule having between 8 and 28 Carbon atoms. In some embodiments of the present methods and kits, the probe can comprise a fatty acid. In some of these embodiments, the probe can comprise a long-chain fatty acid. In some embodiments of the present methods and kits, the probe can comprise 16-DOXYL-stearic acid. In some embodiments of the present methods and kits, the probe can comprise a phospholipid, a lysophospholipid, and/or the like.

In some embodiments of the present methods and kits, the amount of solvent is such that the solvent does not cause or induce significant conformational changes to the carrier proteins. In some embodiments, the amount of solvent may be described as such that the solvent does not cause or induce conformational changes to the carrier proteins. In some embodiments, the amount of solvent is sufficient to increase the concentration of unbound probe in the mixture of aliquot, probe, and solvent to at least 5 times greater than the concentration of unbound probe in a mixture of aliquot and probe without solvent.

In some embodiments of the present methods and kits, the solvent can comprise alcohol. In some embodiments, the solvent can comprise ethanol. In some embodiments, the volume of the amount of solvent can be less than about 30% of the volume of the aliquot. In some of these embodiments, the volume of the amount of solvent can be less than about 25% of the volume of the aliquot. In some of these embodiments, the volume of the amount of solvent can be less than about 20% of the volume of the aliquot. In some of these embodiments, the volume of the amount of solvent can be less than about 15% of the volume of the aliquot. In some of these embodiments, the volume of the amount of solvent can be less than about 10% of the volume of the aliquot. In some of these embodiments, the volume of the amount of solvent can be less than about 5% of the volume of the aliquot.

Some embodiments of the present methods can comprise normalizing the subject binding efficiency to account for the reduction in carrier-protein concentration caused by the amount of solvent in the mixture. In some of these embodiments, the steps of deriving the subject binding efficiency and normalizing the subject binding efficiency can be performed simultaneously.

Some embodiments of the present methods can comprise normalizing the subject binding efficiency to account for the reduction in carrier-protein concentration caused by medical conditions of the patient.

In some embodiments of the present method, the at least one control binding efficiency can comprise a range of control binding efficiencies. In some embodiments, the at least one non-toxic control patient is also healthy.

Some embodiments of the present method can comprise repeating one or more steps of the method for one or more additional aliquots. In some of these embodiments, the amount of solvent mixed with each of the one or more additional aliquots can be different from the amount of solvent mixed with the first or initial aliquot. In some of these embodiments, the subject binding efficiencies derived for the first or initial aliquot and the one or more additional aliquots can be averaged to derive an average subject binding efficiency. In some of these embodiments, the average subject binding efficiency can be compared in the step of comparing the subject binding efficiency to at least one control binding efficiency.

In some embodiments of the present methods and kits, the volume of the aliquot can be less than about 100 µL. In some of these embodiments, the volume of the aliquot can be about 50 µL.

Some embodiments of the present methods can comprise diagnosing, responsive to the subject binding efficiency being less than the at least one control binding efficiency, the subject patient with toxemia.

In some embodiments of the present methods and kits, the probe can be labeled with a spin-label. In some embodiments, the probe can be labeled with a radioactive label. In some embodiments, the probe can be labeled with a fluorescent label. In some embodiments, the extracellular fluid can be blood serum. In some embodiments, the extracellular fluid can be lymph fluid. In some embodiments, the extracellular fluid can be spinal fluid.

Any embodiment of any of the present methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

Figure 1A:
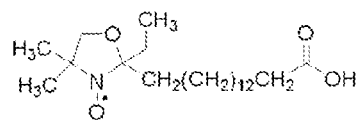
FIGS. 1A-1B depict graphical representations of a number of labeled probes for use in various embodiments of the present methods.
Figure 1A:
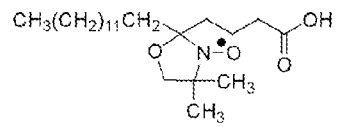
Figure 1A:
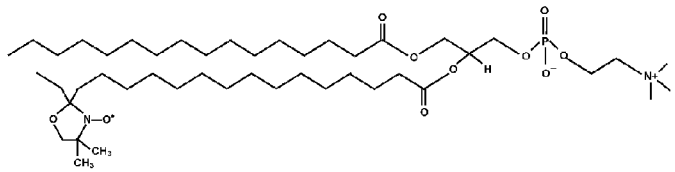

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those steps. Likewise, a step of a method that "comprises," "has," "includes" or "contains" one or more features possesses those one or more features, but is not limited to possessing only those one or more features. For example, in a method that comprises the step of obtaining a sample of blood serum containing carrier proteins, the blood serum includes the specified features but is not limited to having only those features. For example, in such a method, the blood serum could also contain water.

Further, a device or structure that is configured in a certain way is configured in at least that way, but it can also be configured in other ways than those specifically described.

Various embodiments of the present methods may include testing, analyzing, and/or evaluating of a sample of extracellular fluid from a subject patient. For clarity and brevity, embodiments are described below for testing blood serum of a subject patient. However, the embodiments, features, steps, and particulars described below can also be applied to other extracellular fluids such as, for example, lymph fluid, spinal fluid, and the like.

Some embodiments of the present methods include obtaining a serum sample from a subject patient. A serum sample can be obtained, for example, by drawing blood from the patient and using centrifugation to substantially isolate the serum from the blood. Other suitable methods may also be used to obtain the serum sample from the subject patient. An aliquot can also be obtained from this subject sample. Such an aliquot can be separated from the sample or can include the entire sample.

Some embodiments of the present method include mixing a labeled hydrophobic probe with the aliquot. The labeled hydrophobic probe may also be referred to herein as the "labeled probe," the "hydrophobic probe," or the "probe." The probe is (or comprises) an organic molecule, and/or is selected to be capable of binding with (to) carrier proteins (e.g., albumin) of the extracellular fluid (e.g., serum or plasma). In some embodiments, the probe can comprise a suitable number of Carbon atoms. For example, the probe can comprise between 8 and 28 Carbon atoms, including 8, 9, 10, 11, 12, 13, 14, 15, 16, 17, 18, 19, 20, 21, 22, 23, 24, 25, 26, 27, or 28 Carbon atoms, or any smaller range between 8 and 28 Carbon atoms, e.g., between 14 and 22, between 16 and 20, or between 18 and 22 Carbon atoms. In another example, the probe can comprise less than 8 Carbon atoms or more than 28 Carbon atoms. In some embodiments, the probe can comprise a hydrocarbon chain such as, for example, a hydrocarbon chain having any suitable number of Carbon atoms. In some embodiments, the probe can comprise a hydrocarbon molecule whose structure is branched and/or whose structure comprises a ring structure. In some embodiments, the probe can comprise a hydrocarbon molecule comprising elements other than Carbon or Hydrogen, such as, for example, Chlorine, Phosphorous, and/or Nitrogen.

In some embodiments, the probe can comprise a hydrocarbon chain such as, for example, a fatty acid, a long-chain fatty acid, a medium-chain fatty acid, or the like. Examples of probes suitable for some embodiments of the present method include: 16-DOXYL-stearic acid, free radical; 5-DOXYL-stearic acid, free radical; 16:0-16 PC DOXYL, free radical (1-Palmitoyl-2-Stearoyl-(16-DOXYL)- sn-Glycero-3-Phosphocholine); 18:0 PC C13 (1,2-Distearoyl[1-13C]-sn-Glycero-3 -Phosphocholine), Carbon-13 labeled; and Oleic acid-1,2,3,7,8,9,10-13C7, Carbon-13 labeled. Such labeled probes are available from commercial suppliers including, for example, (1) Sigma-Aldrich, Inc., St. Louis, Mo., U.S.A., www.sigmaaldrich.com; (2) TCI America, Portland, Oreg., U.S.A. and Wellesley Hills, Mass., U.S.A, www.tciamerica. com; (3) Fluorochem, Derbyshire, U.K., www.fluorochem. co.uk; and (4) Avanti Polar Lipids Inc., Alabaster, Ala., U.S.A., www.avantilipids.com.

In some embodiments, the probe may be suspended in a volume of liquid so as to, for example, enable accurate measurement of the amount of the probe. This liquid is referred to herein as the "suspension liquid" or "liquid" so as not to be confused with the solvent described herein (even though the suspension liquid may be or comprise a solvent as that term is used in a more general sense). In some of these embodiments, the suspension liquid may be (or comprise) the solvent, which is described below. In some of these embodiments, the probe may be suspended in the solvent in an amount desired for mixing the aliquot, probe, and solvent without further addition of solvent; or may be suspended in an amount of solvent smaller than is desired, such that additional solvent must be separately added to the mixture. For example, if 10 µL of solvent are mixed with a 50 µL aliquot: (1) the probe may be suspended in 10 µL of solvent and the suspension added to the aliquot; or (2) the probe may be suspended in 5 µL of solvent, the suspension added to the aliquot, and 5 µL of solvent (without probe) also mixed with the aliquot. Examples of suitable solution liquids, for use where the probe solution and solvent are mixed while both are liquid, include the materials described below for the solvent.

In others of these embodiments (in which the probe may be suspended in a volume of liquid), the probe solution may be added to a container first and the liquid portion of the liquid/probe solution permitted to evaporate, leaving substantially-only the probe in the container. In such embodiments, the aliquot of serum may then be added such that the probe then dissolves into the serum. Examples of suitable liquids for this suspension/evaporation method include both the liquids described below for the solvent, as well as other liquids (including solvents known in the art as non-polar solvents) that are not miscible with water, such as, for example, methyl ethyl ketone, methyl acetate, diethyl ether, dichloro methane, benzene, pentane, cyclo pentane, etc.

In some embodiments, the amount of probe mixed with the aliquot is sufficient to permit a representative level of binding of the probe to the carrier proteins, i.e., a level of binding that is sufficient to be representative of the binding ability of the carrier proteins in the subject patient's body at the time the sample was taken from the subject patient. In some embodiments, the amount of probe is also small enough to prevent (or to not permit) saturation of the fatty acid binding sites on the carrier proteins. In some embodiments, the amount of probe is such that the molar ratio of probe (that is capable of binding with carrier proteins) to the carrier proteins is between about 0.3 and about 1.5 so as to, for example, encourage binding of the probe carrier proteins in a manner that is representative of the circulatory system of the patient. In some embodiments, the molar ratio of the probe to the carrier proteins is greater than, less then, or between any of about 0.3, 0.4, 0.5, 0.6, 0.7, 0.8, 0.9, 1, 1.1, 1.2, 1.3, 1.4, or 1.5. In other embodiments, the molar ratio of the probe concentration to the carrier-protein concentration can be any suitable ratio that permits the present methods to function as described.

The concentration of carrier proteins in the serum can be approximated from various texts known in the art. In some embodiments, the concentration of carrier proteins can be approximated as the expected concentration of carrier proteins in a healthy patient. In such embodiments, results can later be adjusted (as described below) to account for any reduction in carrier-protein concentration expected as a result of the medical conditions of the patient (e.g., toxemia). In some embodiments, the concentration of carrier proteins can be approximated as the expected concentration of carrier proteins in a patient with the same medical conditions of the subject patient (e.g., toxemia, cancer, and/or the like), and the amount of probe adjusted accordingly so as to, for example, reduce or eliminate the need to adjust results later to account for a reduction in carrier-protein concentration caused by medical conditions of a subject patient.

Some embodiments of the present method include mixing a solvent with the aliquot to, for example, increase the solubility of the hydrophobic probe in the water of the aliquot. As used specifically herein, the "solvent" mixed with the aliquot is a substance (or combination of substances) capable of increasing the solubility of the probe in the mixture (of at least aliquot, probe, and solvent), and can comprise one or more substances generally known in the art as solvents (e.g., polar solvents) and/or one or more substances not generally considered to be solvents (e.g., solids, water-based or other solutions, and the like). In some embodiments, the solvent may include a mixture of two or more substances. In some embodiments, the solvent is selected to be capable of causing some dissociation of the probe from the carrier proteins (e.g., albumin) in the aliquot. In some embodiments, the solvent can be (or comprise) a liquid that is miscible with, or soluble in, water (and/or that may be known in the art as a polar solvent), such as, for example, methanol, ethanol, acetonitrile, dimethyl sulfoxide DMSO), tetrahydrofuran (THF), acetic acid, formamide, ethylene glycol, glycerin, water, and the like. In some embodiments, the solvent may be added at any suitable stage or in any suitable manner, including, for example, to the aliquot alone, to the probe alone, to a mixture of only the aliquot and probe, or to the complete mixture of aliquot, probe, and solvent.

Some embodiments of the present methods include mixing water with any component of the mixture or the entire mixture at any suitable stage, including, for example, to the aliquot alone, to the probe alone, to a mixture of only the aliquot and probe, or to the complete mixture of aliquot, probe, and solvent. Some embodiments of the present methods include mixing additives with the water, with the solvent described above, with any other component of the mixture, and/or or with the complete mixture, to adjust or modify the isotonic properties of the sample mixture. For example, some embodiments of the present method include mixing an amount of NaCl with water to achieve a concentration of about 0.9% NaCl to simulate the isotonic properties of blood and the normal cells of the body, as may be done in other areas of medicine and biological sciences.

In some embodiments where the solvent is selected to be capable of causing dissociation of the probe from the carrier proteins (e.g., albumin), the amount of solvent added to the aliquot is such that a portion of the probe is dissociated from (caused to not bind or stop binding with) the carrier proteins without causing significant dissociation of toxins from the carrier proteins. As used here, "significant dissociation of toxins" is dissociation from carrier proteins that substantially affects the representative nature of the binding properties exhibited by the carrier proteins in the aliquot (relative to the binding properties the same carrier proteins exhibited in the subject patient's body at the time the sample was obtained from the subject patient). This lack or relatively minimal amount of dissociation of toxins may also be described as, simply, "without causing dissociation of toxins." As used here, "without causing dissociation of toxins" does not necessarily mean that no toxins are dissociated from carrier proteins, and in fact, some toxins may be dissociated from carrier proteins. Instead, as used here, "without causing dissociation of toxins" means that the binding properties exhibited by the carrier proteins in the aliquot are still representative of the binding properties the same carrier proteins exhibited in the subject patient's body at the time the sample was obtained from the subject patient).

In such embodiments, and in contrast to U.S. Pat. No. 7,166,474 (described above in background section), the amount of solvent added to the aliquot is also such that the solvent does not induce significant conformational changes to the carrier proteins. As used here, "significant conformational changes" are conformational changes to the carrier proteins that substantially affect the representative nature of the binding properties exhibited by the carrier proteins in the aliquot (relative to the binding properties the same carrier proteins exhibited in the subject patient's body at the time the sample was obtained from the subject patient). For example, a conformational change would substantially affect the representative nature of the binding properties if it caused the carrier proteins to release toxins so as to bind a measurably greater amount of probe than the carrier proteins would have bound without such conformational changes. This lack or relatively minimal amount of conformational changes in carrier proteins may also be described as, simply, "without causing (or inducing) conformational changes to the carrier proteins" or "does not cause (or induce) conformational changes to the carrier proteins." As used here, this does not necessarily mean that no conformational changes are caused to or induced in the carrier proteins, and in fact, some conformational changes may occur. Instead, as used here, "without causing conformational" and/or "does not cause conformational" mean that the binding properties exhibited by the carrier proteins in the aliquot are still representative of the binding properties the same carrier proteins exhibited in the subject patient's body at the time the sample was obtained from the subject patient).

In some embodiments, the amount of solvent is such that the concentration of unbound (free) probe in the mixture (of aliquot, probe, and solvent) is at least a multiple greater than (e.g., 5, 6, 7, 8, 9, 10, 20, 50, 100, 500, 1000, 5000, 10000, or 100000 times greater than) the concentration of unbound (free) probe before the addition of the solvent (e.g., in a mixture of only the aliquot and probe). In other embodiments, the amount of solvent is such that the concentration of unbound (free) probe in the mixture (of aliquot, probe, and solvent) is in a range between about a lower multiple and about a higher multiple greater than (e.g., between about 5 and about 10, between about 10 and about 100, or between about 100 and about 1000 times greater than) the concentration of unbound (free) probe before the addition of the solvent (e.g., in a mixture of only the aliquot and probe).

In some embodiments, the volume of the amount of solvent mixed with the aliquot is a percentage of the volume of the aliquot. For example, for a 50 µL aliquot, the volume of solvent added may be between about 1% and about 30%, i.e., between about 0.5 µL and about 15 µL, or in any individual percentage or range of percentages within this range, e.g., about 10%, about 20%, between about 5% and about 20%, between about 10% and about 20%, or the like. In some embodiments, the volume of solvent mixed with the aliquot is greater than about and/or less than about any of: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30%. In some embodiments, a specific volume of solvent mixed with the aliquot is within this range, such as, for example, for an aliquot of 50 μL, about 1 μL, about 5 μL, about 10 μL, about 15 μL, about 20 μL, or any other suitable volume of solvent can be added.

The addition of solvents in such amounts can reduce variations and/or errors by largely overcoming the influence of stochastic factors such as, for example, influences caused by various trace substances in the aliquot. For example, an aliquot of serum may have trace amounts of alcohol that vary significantly relative to trace amounts of alcohol in a different aliquot of serum. Such significant relative differences may introduce variations that can affect the repeatability and reliability of the results achieved. By adding the solvent (in an amount to achieve the effects described above) prior to analyzing the mixture, and then adjusting the results to account for the concentration of the added solvent (e.g., to normalize the results by negating the effects on bound- and unbound-probe concentrations caused by the added solvent), the relative significance of such variations can be reduced. This reduction in relative significance can increase the repeatability and reliability of the results achieved by the present methods.

In some embodiments, the probe and the solvent can be mixed together prior to mixing either of the probe or solvent with the aliquot. In some embodiments, a surfactant may also be added to the mixture to promote, encourage, or assist the binding of probe to the carrier proteins in the aliquot of serum. In such embodiments, the surfactant may be added at any suitable stage or in any suitable manner, including, for example, to the aliquot alone, to the probe alone, to a mixture of only the aliquot and probe, or to the complete mixture of aliquot, probe, and solvent. Examples of suitable surfactants include nonionic detergents such as Tween 20 and Triton X-100, which may be available from suppliers such as Sigma-Aldrich, Inc., St. Louis, Mo., U.S.A., www.sigmaaldrich.com. Some embodiments of the present methods may include incubating the mixture (of probe, solvent, and aliquot of serum) for a period of time including, for example, greater than or less than about any of 10, 9, 8, 7, 6, 5, 4, 3, 2, or 1 minutes. Some embodiments of the present methods may include agitation of the mixture (e.g., by shaking, or by shaking at between, greater than, less than, or between about 5 and 8 Hz for a period of time that can be separate from or at least partially (including wholly) concurrent with the incubation, including, for example, less than about any of 10, 9, 8, 7, 6, 5, 4, 3, 2, or 1 minutes. Additionally, some embodiments may include incubating and/or agitating the mixture at about a predetermined temperature such as, for example, 37° C. (approximate human body temperature), or the like. In other embodiments, the mixture can be agitated and/or incubated for any suitable period of time, at any suitable frequency, and/or at any suitable temperature.

As described in more detail below, some embodiments of the present method include analyzing the mixture of the aliquot, probe, and solvent to determine the binding efficiency of carrier proteins including, for example, as a function of concentrations of residual-free and protein-bound fractions of the probe in the aliquot (adjusted for the added solvent by multiplying by the factor inversely proportional to solvent concentration). As an example, some embodiments include measuring the concentration of each of the protein-bound and unbound (free) fractions of the probe, and the binding efficiency derived from these concentrations (and adjusted for the change in concentration caused by the addition of the solvent). The presence of toxemia is indicated if, in the subject sample (aliquot), the binding efficiency of carrier proteins is reduced relative to a control range exhibited by carrier proteins in non-toxemic control subjects, and if the degree of reduction in binding efficiency is higher than the reduction of carrier-protein concentration. In some embodiments, the reduction in binding efficiency can be normalized to account for the reduction in carrier-protein concentration, such that the normalized binding efficiency can be compared directly to the control range. The control subjects may be any one subject or group of subjects suitable for comparison, including, for example, one or more non-toxemic ICU patients, non-toxemic subjects, healthy subjects, or the like.

Investigations of solutions of carrier proteins have revealed that the binding constant Kb (which may also be known in the art as the inverse of the dissociation constant or as the ratio of the association and dissociation coefficients) of carrier proteins (e.g., albumin) in hydrophilic solution, e.g. serum, with respect to hydrophobic substances (e.g., binding of long chain fatty acids to serum albumin), can be reduced by the addition of a solvent (e.g., alcohol), as illustrated by the linear function of the inverse of solvent concentration:

$$Kb = K \cdot (Sc/S - 1) \qquad (1)$$

where Kb is the binding constant, S is the solvent concentration, Sc is the critical concentration of the solvent in a solution at which the probe is completely soluble (will completely dissociate from the carrier proteins and dissolve in the solution), and K is the constant equal to binding constant Kb in a solution containing the solvent at concentration of Sc/2. One possible explanation for this is that hydrophobic forces in hydrophilic solutions are functions of the entropy and the enthalpy of the solution, and the introduction of such solvents can modify each of the entropy and the enthalpy of the solution, in some instances, for example, as a linear function of solvent concentration.

Without the addition of solvent to the aliquot, other factors such as, for example, concentrations of various metabolites and serum proteins, temperature, pH variations, and the like, can influence the entropy of the water medium and cause significant variations in the hydrophobic forces in the aliquot. This can result in variations in the concentration of the unbound (free) fraction of the hydrophobic probe. In contrast, the addition of an amount of solvent that increases the concentration of unbound probe in the mixture (of aliquot, probe, and solvent) to at least 5 times greater than the concentration of unbound probe before the addition of the solvent (e.g., a mixture with only the aliquot and probe) can overcome the influence of stochastic factors on the aliquot, and thereby significantly reduce variations in measured results down, for example, to 20% or less.

Concentrations of protein-bound and unbound (free) fractions of the probe can be measured by any suitable methods or techniques. For example, the concentrations of protein-bound and unbound (free) fractions of the labeled probe in the mixture of the aliquot, probe, and solvent can be measured by: measurement of radioactivity (e.g., where the probe has a radioactive label, such as Carbon-13), fluorescence spectroscopy (e.g., where the probe has a fluorescent label), EPR-spectroscopy (e.g., where the probe has a spin label), luminescent spectroscopy (e.g., where the probe has a luminescent label), or the like. However, without the addition of polar solvent at a relatively low concentration in the aliquot, the concentration of unbound-free probe in the aliquot may be below a minimal concentration measurable with such methods of measurements. Some embodiments of the present methods include mixing a solvent with the aliquot, where the amount (volume, concentration, or the like) is such that the solvent does not induce significant conformational changes to carrier proteins in the aliquot and/or significant dissociation of protein-bound metabolites and toxins. In some embodiments, the amount of solvent is such that the concentration of unbound probe in the mixture is increased to a level sufficient for accurate measurement by the method of measurement used. For example, in some embodiments, the amount of solvent mixed with the aliquot is the smallest amount necessary to increase the concentration of unbound probe in a mixture of probe, aliquot, and solvent to at least about five times greater than the concentration of unbound probe in a mixture of only the same probe and aliquot.

Some embodiments of the present method can include one or more intermediate or preparation steps for preparing the mixture after mixing the aliquot, probe, and solvent but before measuring the concentrations of protein-bound and unbound (free) fractions of the probe. For example, for probes having radioactive or fluorescent labels, the mixture can be incubated in a dialysis tube divided into two volumes by a membrane that is permeable to the probe but not permeable to carrier proteins in the mixture so as to separate the mixture into two portions, a first portion containing carrier proteins and unbound probe, and a second portion containing unbound probe but substantially no carrier proteins. After this incubation, the probe concentration can be measured for each of the carrier-protein-containing and carrier-protein-free portions of the mixture. Measurement of the concentrations of protein-bound probe and/or unbound probe depends of the type of labeled probe used. The first separated portion can be analyzed using either measurement of radioactivity or fluorescence, as appropriate to the type of labeled probe. If the measurement method is unsuitable for direct measurement of free probe (e.g., spectroscopy of some fluorescent labels), the second separated portion can be mixed with a portion of carrier proteins and the concentration of the previously-unbound probe analyzed similar to the portion of protein-bound probe as it is described above.

By way of another example, for a spin-labeled probe, the mixture can be analyzed using an EPR-spectrometer to obtain an EPR spectrum of the probe such that the EPR spectrum is simultaneously indicative of different spectral components corresponding to protein-bound and free fractions of the probe. More specifically, spectral analysis of the EPR-spectrum can permit separation of single spectral components, identification of their relation to protein-bound and unbound fraction of spin probe, and approximation or estimation of their relative concentrations.

Binding efficiency (BE) of the carrier proteins is the concentration ratio of bound probe and unbound probe. In some embodiments of the present methods, binding efficiency is derived, calculated, or otherwise determined once the mixture of aliquot, probe, and solvent has reached binding equilibrium (with respect to the binding of probe to carrier proteins). Binding efficiency (BE) and/or BE parameters of serum carrier proteins can be calculated using the protein-bound probe concentration (B) and unbound probe concentration (F), and solvent concentration (S) in the mixture. For example, BE can be calculated with either:

$$1BE = (Sc/S - 1) \cdot (F/B) \cdot P \quad (2)$$

OR $$1/BE = (Sc/S - 1) \cdot (F/B) \cdot P \cdot (N - B/P) \quad (3)$$

where Sc (specified above), P is the concentration of carrier proteins in the sample, and N is the number of binding sites for the probe on the carrier protein molecule.

Formula (3), above, differs from Formula (2) by a factor (N−B/P) that adjusts for the effect of binding saturation. For some serum samples, in which carrier proteins are mostly presented by serum albumin, generally N=7 and the factor (N−B/P) is generally close to 6.

In some embodiments, a toxin evacuation parameter (TEP) can be derived, calculated, or otherwise determined for the carrier proteins, as an alternative or in addition to the binding efficiency BE. The toxin evacuation parameter can be indicative to the ability of the carrier proteins to bind toxins relative to the ability of the carrier proteins to release bound toxins, and can be calculated as the square of binding efficiency (BE):

$$TEP = BE \cdot BE = BE^2 \quad (4)$$

The present methods were performed for non-toxemic control patients to determine control values for non-toxemic (and/or healthy) patients, including control values such as mean and a range of normal variation. The mean BE of the control patients was assigned a value of 100%. The control range of BE variation in healthy control patients was between about 40% and about 160%. In some embodiments, the control range used for comparison to the BE of the subject patient may be any suitable value or subset range between about 40% and about 160% including, for example, between about 50% and about 150%, between about 40% and about 100%, or the like. In some embodiments, a control value may be used (where a subject patient's BE below the control value indicated the presence or likely onset of toxemia). In such embodiments, the control value used may be any suitable value between about 20% and about 160%, including, for example, 20%, 25%, 30%, 35%, 40%, 43%, 45%, 50%, 55%, 60%, 65%, or any other suitable value in the disclosed range. In some embodiments, different control values can indicate, and/or can be used to diagnose, varying degrees of risk. For example, a BE above 40% can indicate a low risk of having or developing toxemia, a BE between 20% and 40% can indicate a moderate risk of having or developing toxemia, and a BE below 20% can indicate a high risk of having or developing toxemia. In some embodiments, BE can be calculated relative to (as a percentage of) the mean value of the control range.

As discussed above, the presence of toxemia can be indicated if, in the subject aliquot, the binding efficiency (BE) of carrier proteins is reduced relative to the control range or value, and if the degree of reduction in BE is higher than the reduction of carrier-protein concentration from a carrier-protein concentration that would be expected in control patients. For example, the concentration of carrier proteins may be reduced by the addition of solvent; and the accuracy of the derived BE can be improved if the derived BE is adjusted for this reduction. By way of another example, the concentration of carrier proteins may be reduced (relative to a healthy patient) in a subject patient with toxemia; and the accuracy of the derived BE can be improved if the derived BE is adjusted for this reduction. Reduction in carrier-protein concentration will not always be known exactly, and adjustment for reduction in carrier-protein concentration (that may result from several sources) can be approximated from various data, e.g., expected concentrations of carrier proteins for healthy and/or toxemic patients.

Some embodiments of the present methods can comprise diagnosing a patient with toxemia response to, for example, the BE of the subject patent being lower than a control value or range of BE. Some embodiments of the present methods can comprise transmitting a comparison of the subject BE and the control BE value or range to a clinician, physician, or the like, including, for example, a doctor that is responsible for diagnosing the subject patient. Some embodiments of the present methods can comprise transmitting a comparison of the subject BE and control BE value or range to an insurance carrier of the subject patient. Some embodiments of the present methods may comprise using the BE or other parameters derived for a subject patient to monitor the efficiency and/or efficacy of hemosorption, hemodialysis, antiseptic treatments, antibiotic treatments, anti-inflammatory treatments, and/or other therapies or treatments. Some embodiments of the present methods can comprise testing blood, plasma, plasma products and/or albumin solutions prior to injection or infusion of such plasma products or albumin solutions into a patient. Some embodiments of the present methods can comprise evaluating or monitoring a patient's response to hemosorption, hemodialysis, antiseptic treatments, antibiotic treatments, anti-inflammatory treatments, and/or other therapies or treatments. Some embodiments of the present methods can comprise testing or evaluating the health of a subject patient to assess the patient's readiness or suitability for a task, assignment, and/or deployment, such as, for example, submarine duty, military deployment, specific line of employment, and/or specific tasks or group of tasks, deployment or assignment in medical wards or toxic cleanup activities where the risk of exposure toxins may be high.

Some embodiments of the present methods may include using the results for triage purposes such as determining whether and when to treat various patients relative to each other. For example, where there are three patients, one with a BE of 2%, one with a BE of 10%, and one with a BE of 15%; the patient with a BE of 2% may be too ill to have a reasonable likelihood of recovery; and the patients with BEs of 10% and 20% may both have a reasonable likelihood of recovery, but the patient with a BE of 10% may have a more immediate need for treatment to capitalize on the reasonable likelihood of recovery. In such a situation, if resources are limited, the patient with a BE of 10% can be treated first, the patient with a BE of 20% can be treated second, and the patient with a BE of 2% can be treated last (if sufficient resources are available) or may be comforted with pain killers or the like.

Some embodiments of the present methods can comprise evaluating the viability of donor organs (e.g., liver, kidney, or the like) by testing a sample of the donor's blood serum or other extracellular fluid. Some embodiments of the present methods can comprise evaluating the competence (health and/or functionality) of transplanted organs (e.g., liver, kidney, or the like) in patient's body. Some embodiments of the present methods may comprise evaluating a competence of patient's protective (immune) system in response to exotoxins (e.g., snake venom, poisons, food poisoning, or the like). Some embodiments of the present methods may comprise evaluating blood derivatives (e.g., donated whole blood, plasma, serum, or the like) for carrier-protein competence (health or functionality), carrier-protein deficiencies, and/or the like.

Example of EPR Spectroscopy

Figure 4:
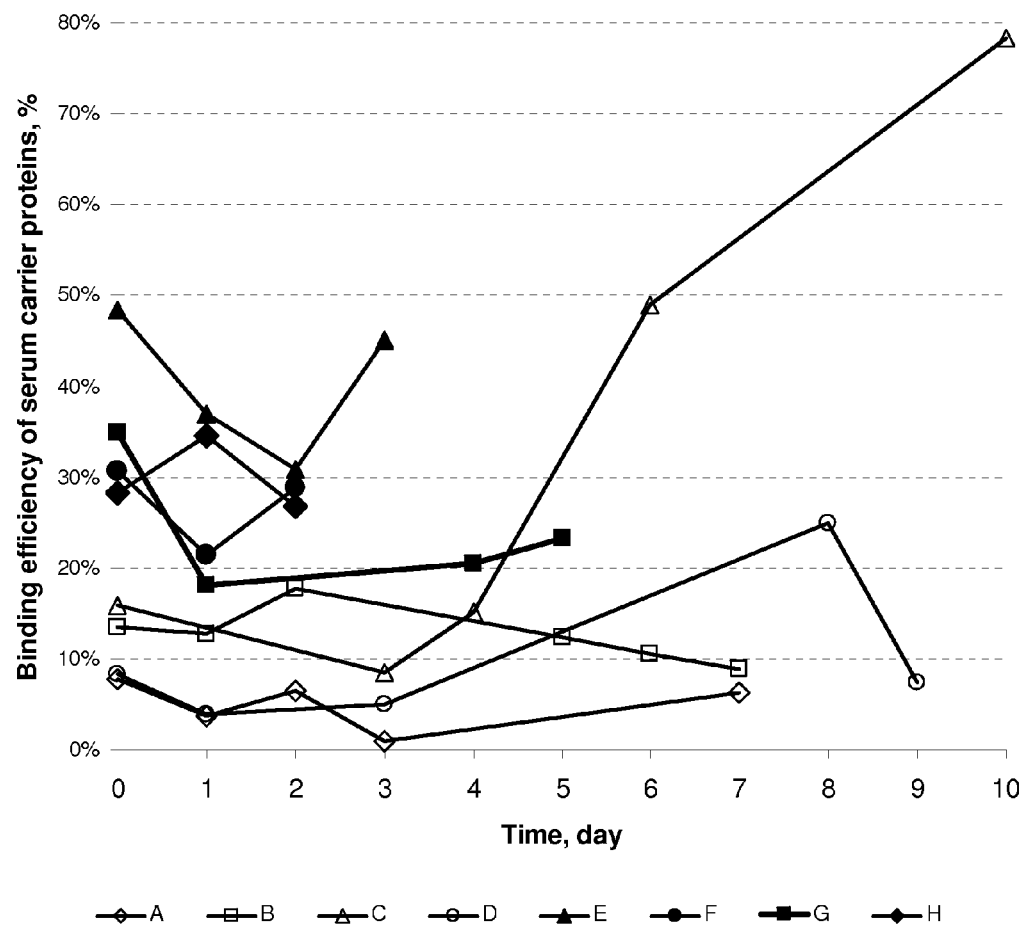
FIG. 4 depicts a graphical representation of the binding efficiency of serum carrier proteins, as assessed by the present methods, for a number of patients admitted to an intensive care unit (ICU).

Some embodiments of the present methods can use EPR spectroscopy to analyze the mixture of aliquot, probe, and solvent (some of which probe is generally bound to carrier proteins in the aliquot). One example of a suitable labeled probe is depicted in FIG. 4, which depicts a suitably labeled stearic acid molecule, 16-doxyl stearic acid. The mixture can be placed into the EPR spectrometer and exposed to both a high magnetic field and microwave power, and various properties (such as the properties described herein) of the mixture measured (directly or indirectly).

1. Binding of Spin-Labeled Probe to Carrier Proteins in the Sample

Figure 1B:
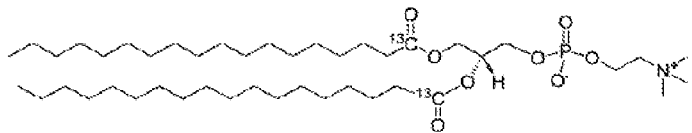
Figure 1B:
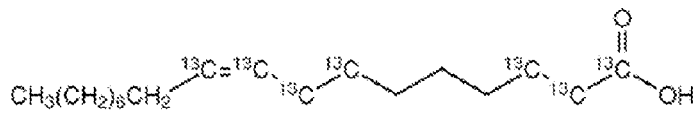
Figure 1B:
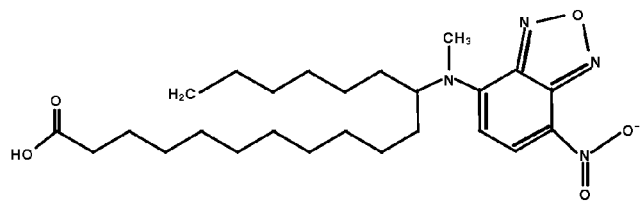
Figure 1B:
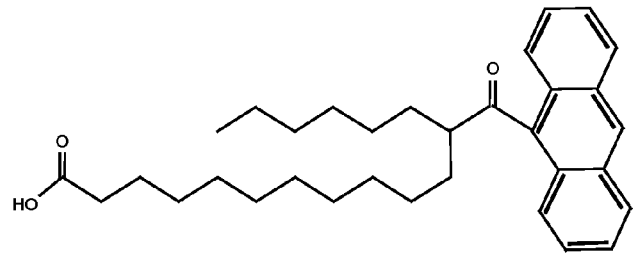

Spin-labeled fatty acid probes (e.g., as shown in FIG. 1A-1B) can be used to study carrier proteins by EPR spectroscopy. Spin-labeled fatty acid probes may also be referred to herein as "fatty acid probes" (and more generally "labeled probes" or "probes"). One exemplary procedure includes mixing an amount of labeled fatty acid probe (e.g. 16-doxyl stearic acid, a fatty acid labeled with a nitroxide radical) with a small (i.e., 50 µl) amount of serum or plasma. The molar ratio of the probe to carrier proteins (e.g., albumin) can be in the range between about 0.3 and about 1.5 so as to, for example, permit a level of binding that is sufficient to be representative of the binding ability of the carrier proteins in the subject patient's body at the time the sample was taken from the subject patient while preventing saturation of the fatty acid binding sites on the carrier proteins. The labeled probe can also be mixed with a polar solvent such as, for example, ethanol. The binding affinity of carrier proteins for the labeled probe can be reduced by the ethanol to increase the number of unbound probe molecules in the mixture, as described above. After mixing the probe and solvent with the aliquot of serum, the resultant mixture can be incubated with constant agitation (e.g., at 5-8 Hz) for 10 min at 37° C.

Figure 2:
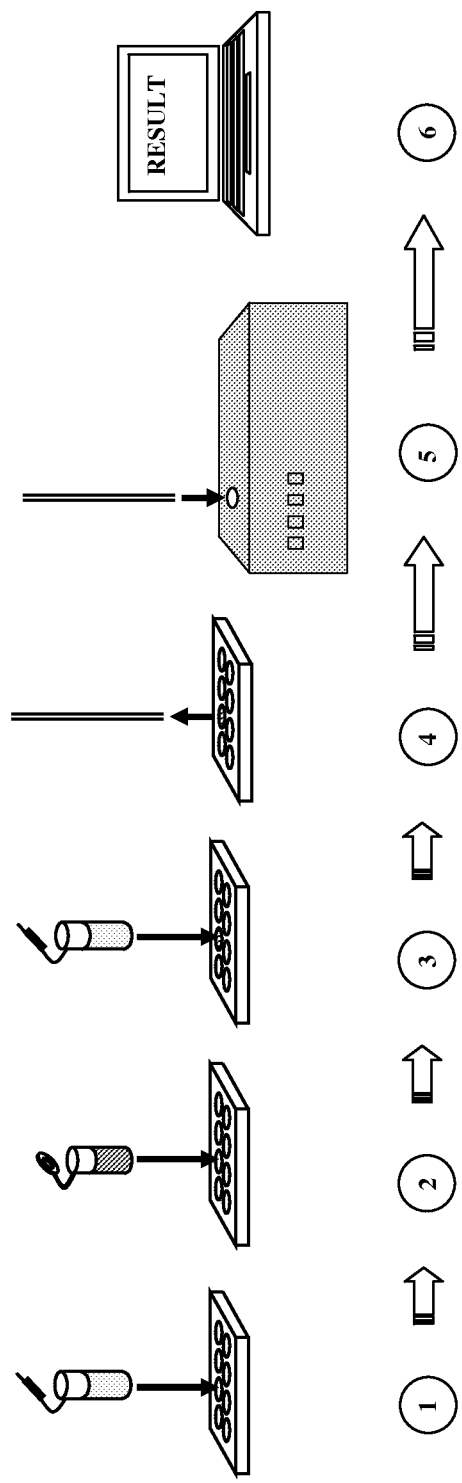
FIG. 2 depicts a schematic representation of one exemplary procedure for evaluating a mixture containing an aliquot of serum and an amount of labeled probe by EPR spectroscopy that is suitable for use in embodiments of the present methods.

This exemplary procedure is schematically depicted in FIG. 2. The embodiment of the present methods depicted in FIG. 2 includes: (1) placing the probe into a container, (2) mixing an aliquot of serum with the probe in the container, (3) mixing solvent with the aliquot and probe in the container, (4) placing the mixture (of aliquot, probe, and solvent) into a pipette (before or after incubation), (5) placing the pipette into, and analyzing the mixture with, the EPR spectrometer to obtain EPR spectra of the mixture, and (6) processing the measurements to obtain the concentrations of protein-bound and unbound probe, and determining the binding efficiency of the carrier proteins in the serum of the aliquot. The steps and/or order of steps depicted and/or described in this embodiment of the present methods are not intended to be limiting. Other embodiments of the present methods may omit any of these steps, and/or may include other steps, may include any combination of these or other steps in any suitable order.

Interaction between the stearic acid probe and serum carrier proteins may be mostly specific to albumin. The affinity of albumin for 16-doxyl stearic acid (the labeled probe) may generally be similar to its affinity for unlabeled stearic acid (which may be relatively high, e.g., a binding constant of about $10^9$ mol$^{-1}$). In blood serum of a healthy patient (and in the absence of binding site saturation), the abundance of albumin relative to other serum proteins and the presence of several high-affinity binding sites for long chain fatty acids may result in 99% or more of the stearic acid probe being bound exclusively to albumin.

2. Instrumentation

Following incubation of the probe with the sample, an amount of the mixture can be placed into a glass capillary tube. The tube can then be inserted into an EPR spectrometer (e.g., Model No. EPR 01-08 available from MedInnovation GmbH, Wildau, Germany). In the EPR spectrometer, the mixture is exposed to both a high magnetic field and microwave power. This exposure induces resonance of the spin label and absorption of microwave power. An EPR spectrum can thereby be generated by scanning measurements of the magnetic field strength and absorption of microwave power. Other EPR spectrometers, such as conventional X-Band EPR spectrometers, or other EPR spectrometers operating with a microwave frequency of approximately 9-10 GHz, can be also used for obtaining these measurements. The sample can be maintained at 37° C. during the measurement process to mimic physiologic conditions.

3. Data Processing

The EPR spectrum obtained with the spin probe can be analyzed using a simulation process. Simulation can be performed using least-square fitting of a model spectrum to the measured spectrum. In this way, the EPR spectrum of the spin probe can be calculated using the appropriate model and parameters of the site where the spin probe is situated.

The EPR spectrum obtained will generally consists of a large set of data points containing some amount of measurement noise or error. If the parameters of the binding site model are accurately established, an ideal experimental spectral curve can generally be derived. This task may be more complex when there are several sites that can bind the spin probe. In this situation, these different binding sites can be considered to improve accuracy when deriving the model spectrum. A number of different tools have been developed that enable the derivation of a composite model spectrum for compounds that possess several binding sites for the spin probe.

Figure 3:
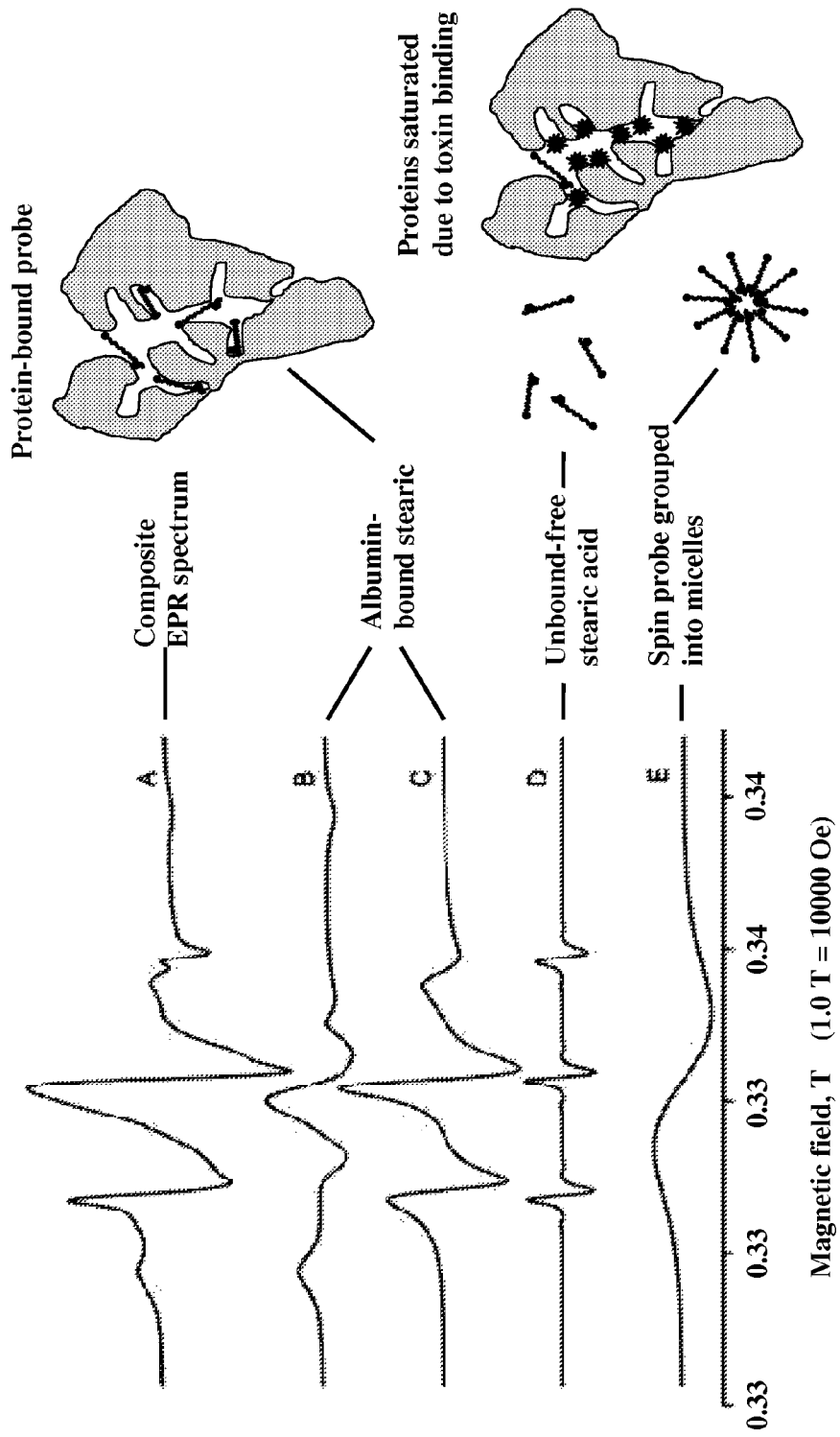
FIG. 3 depicts an exemplary EPR spectrum of a mixture of serum and a spin-labeled fatty acid probe (16-doxyl stearic acid) obtained by an EPR spectroscopy method of analysis that is suitable for use in embodiments of the present methods.

Analysis of the EPR spectrum generated from the stearic acid probe bound to albumin (as described above) reveals four distinct spectral components. The major portion of the spectrum is represented by two components, as represented by lines B and C in FIG. 3. Each of these major spectra components is representative of the portion of fatty acid probe bound to carrier proteins (e.g., albumin) (as may correspond to the pictorial representation of carrier proteins capable of binding with (to) the probe). The two remaining components are representative of free or unbound fatty acids present in the solution. The unbound fatty acids may be present singularly in solution, as represented by line D in FIG. 3 (as may correspond to the pictorial representation of a carrier protein that is saturated by toxins), or may be organized into clusters of fatty acid micelles, as represented by line E in FIG. 3. The process of simulation generally determines the values of ideal spectrum parameters representing the equation that provides the best curve fit of the simulated and measured spectra. These parameters can include the intensity of each spectral component as well as specific EPR parameters determining the position, width, and shape of spectrum lines.

Each EPR spectrum reflects the structural and functional characteristics of the protein that impact the binding of the probe to albumin. One technique that is employed for the generation of EPR spectra includes a sample mixture (of serum aliquot, probe, and solvent). The characteristics of albumin that can be assessed from the EPR spectrum that is generated can include the concentration of the fatty acid probe that is bound to albumin, and the concentration of unbound probe. Another characteristic that can be generated is an estimation of changes in protein conformation (significant conformational changes are prevented and/or minimized in the present methods) at the albumin binding site for fatty acids (certain parameters of the EPR spectrum indicate the mobility of the fatty acid probe at its binding site on albumin; such mobility can be influenced by several parameters, and those parameters can be used to prove an absence of significant conformational changes of albumin molecule due to excessive concentration of a polar solvent in a sample mixture).

Exemplary Data Obtained Through Testing of the Present Methods

The present methods have been tested on ICU-patients suffering from post-surgery diseases and on healthy subjects. The common methods employed in this testing are discussed first, and the results of this testing on several specific cases are discussed below. The samples tested were obtained at the intensive care unit (ICU) of the Blokhin Russian Oncological Scientific Center of the Russian Academy of Medical Science, Moscow, Russia. These samples were then frozen at −30° C., and later investigated by the inventor of the present methods.

Blood serum was obtained by whole blood centrifugation. An aliquot of 50 µl of serum from each patient was used for each test. A spin probe of 2-(14-carboxytetradecyl)-2-ethyl-4,4-dimethyl-3-oxazolidinyloxy (purchased from Fluorochem Ltd., Derbyshire, UK) was mixed into the aliquot at a concentration of 0.58 mmol/l. A solvent, 10 µl of ethanol, was mixed into the aliquot. The mixture was then incubated for 10 min at 37° C. with continuous agitation in a standard shaker operated at about 5-8 Hz.

After incubation, the probe was placed into a glass capillary (e.g., Model No. RM-40, available from KABE LABORTECHNIK GmbH, Numbrecht-Elsenroth, Germany).

The EPR spectrum of the mixture was then measured, as described below. The above-described capillary was placed into the resonator of an EPR spectrometer for spectroscopic analysis. The spectroscopy parameters were as follows: microwave power 15 mW at frequency 9.32 GHz; magnetic field 3325 G with scan range 120 G; modulation amplitude 2 G; data accumulation by three scans each with 4096 measured points and a sweep time 60 s. The capillary temperature was 37° C., and was controlled within +/−0.2° C.

The EPR spectrum was analyzed by computer using an EPR-spectrum simulation with nonlinear least-squares fits. The spectrum model included five components. The first two are the S and W components which represent portions of the probe that were bound differently on carrier proteins. As shown here, the S and W components primarily differed by spectral parameters of A tensors (hyperfine splitting tensor): $A_\parallel(S)$=30.02 Oe, $A_\perp(S)$=9.02 Oe, $A_\parallel(W)$=21.5 Oe, and $A_\perp(W)$=13.35 Oe. Parameters of the g tensor used in the spectral calculations of these two components were: $g_\parallel(S)$= 1.9983, $g_\perp(S)$=2.0019, $g_\parallel(W)$=1.9990, and $g_\perp(W)$=2.0013. The third F component represented the unbound spin probe residing free in the sample. The parameters of the F component were: $A_\parallel(F)$=$A_\perp(F)$=15.6 Oe, and $g_\parallel(F)$=$g_\perp(F)$=2.0008. The width of spectrum line for the F component, $L(F)$=0.42 Oe, was significantly different from the width of the spectrum line for the S and W components, $L(S)$=$L(W)$=3.45 Oe. The fourth and fifth components represented minor fractions of the probe that were not related to protein-bound or unbound-free probe, but to the probe molecules aggregated into micelles (M) and ones associated with free-lipids (P). The parameters of the M component were: $A_\parallel(M)$=$A_\perp(M)$=0, $g_\parallel(M)$=$g_\perp(M)$=2.0014, and $L(M)$=11.96 Oe. The parameters of the P component were: $A_\parallel(P)$=$A_\perp(P)$=14.2 Oe, $g_\parallel(P)$=$g_\perp(P)$=2.0012, and $L(P)$=1.1 Oe. The considering of the M and F components in the spectrum model can improve accuracy of the analysis of concentrations of protein-bound and unbound-free probes, but is not necessarily required in embodiments of the present methods.

During the EPR-spectrum simulation with nonlinear least-squares fits, relative concentrations of all spectral components as well as precise values of spectral parameters were determined. At the specified ethanol concentration, the majority of the (spin) probe, i.e., 90 to 99%, was found to be bound on carrier proteins (mostly on serum albumin, which generally makes up about 90% of the total carrier proteins in serum). The unbound fraction of the spin probe was found to have a relative concentration of 0.5 to 10%, and was found to vary somewhat among samples of different patients, and among different samples taken under different clinical conditions (clinical statuses) of the same patient.

FIG. 4 depicts the results of this analysis of binding efficiency of carrier proteins in serum of eight different patients (A-H, described below) suffering from post-surgery disease, observed during the time the patients were administered in the ICU.

(A) Patient with Septic Shock

Clinical diagnosis: Patient A was diagnosed with lymphoma, septic shock, acute respiratory failure, and acute kidney failure.

Microbiological data: Candida alb and Candida spp were discovered in pleural cavity.

From the time of Patient A entered the ICU, binding efficiency (BE) was drastically reduced to the range of about 2-10%, and remained very low (as illustrated by line A in FIG. 4). Dysfunction of the toxin evacuation of serum carrier proteins in Patient A was observed in the early stages of the sepsis-related toxemia. Patient A expired.

(B) Patient with Severe Sepsis

Clinical diagnosis: Patient B was diagnosed with severe sepsis, general peritonitis and intestinal haemorrhage.

Microbiological data: *Pseudomonas aeruginosa* was discovered in bronchoscopy and drainage.

BE for patient B was initially reduced and gradually decreased (as illustrated by line B in FIG. 4). Patient B expired.

(C) Patient with Sepsis

Clinical diagnosis: Patient C was diagnosed with sepsis and hepatic failure.

Microbiological data: Cholangiostoma—*E. faecium* was discovered in drainage.

Binding efficiency (BE) was drastically reduced compared the control range. Specifically, BE for Patient C was reduced to about 10% as a result of sepsis-related toxemia (as illustrated by line C in FIG. 4). Patient C was treated with antibiotic therapy, and was significantly rehabilitated by the sixth (6th) day following admission to the ICU. BE for Patient C varied (and largely correlated to) the course of treatment, e.g., BE was lower initially and increased with the reduction of toxemia caused by the antibiotic therapy. Patient C was successfully discharged from the ICU on the tenth (10th) day after admission.

(D) Patient with Severe Sepsis

Clinical diagnosis: Patient D was diagnosed with severe sepsis, peritonitis, bilateral pneumonia, chronic renal failure, and liver failure.

Microbiological data: Sputum—Ps. *aeruginosa*, Acinetobacter, *Candida* alb were discovered.

Drastic reduction of binding efficiency (BE) was observed on the first day of admission to the ICU (as illustrated by line D in FIG. 4). Patient D was treated with antibiotic therapy, and was partially rehabilitated by the eighth (8th) day following admission to the ICU, however, at the ninth (9th) day, acute exacerbation from liver failure and thrombocytopenia occurred that debilitated the patient. Patient D expired.

(E) Patient Who Did Not Exhibit Outward Signs of Toxemia

Clinical diagnosis: Patient E was diagnosed with partially compensated respiratory failure.

Binding efficiency (BE) remained relatively high (compared to toxemic patients) during the time of observation (as illustrated by line E in FIG. 4). Patient E was successfully discharged from the ICU on the fourth (4th) day after admission.

(F) Patient Who Did Not Exhibit Outward Signs of Toxemia

Clinical diagnosis: Patient F did not show complications during the period of time of his administration in the ICU.

Binding efficiency (BE) remained relatively high (compared to toxemic patients) during the time of observation (as illustrated by line F in FIG. 4). Patient F was successfully discharged from the ICU.

(G) Patient Who Did Not Exhibit Outward Signs of Toxemia

Clinical diagnosis: Patient G did not show complications during the period of time of his administration in the ICU.

Reducing binding efficiency (BE) observed at second day after admission, then parameter BE showed gradual increase during following period of time and remained relatively high (compared to toxemic patients) from fourth (4th) day on (as illustrated by line G in FIG. 4). Patient G was successfully discharged from the ICU on the sixth (6th) day after admission.

(H) Patient Who Did Not Exhibit Outward Signs of Toxemia

Clinical diagnosis: Patient H diagnosed with nephropathy and partially compensated respiratory failure combined with Chronic Obstructive Pulmonary Disease.

Binding efficiency (BE) remained relatively high (compared to toxemic patients) during the time of observation (as illustrated by line H in FIG. 4). Patient H was successfully discharged from the ICU on the third (3rd) day after admission.

(J) Healthy Person

Volunteer J observed to be without evidence of any diseases.

Binding efficiency (BE) for volunteer J is omitted from FIG. 4 for clarity. However, BE for volunteer J remained at approximately 120% at the time of observation.

(K) Healthy Person

Volunteer K observed to be without evidence of any diseases

Binding efficiency (BE) for volunteer K is omitted from FIG. 4 for clarity. However, BE for volunteer K remained at approximately 100% at the time of observation.

Analysis of the clinical relevance of the parameter BE (as measured for these patients with the present methods) indicated that significant reduction of binding efficiency (BE) indicated a high probability of a subject patient developing toxemia two days earlier than other known laboratory parameters and clinical indices. The changes in BE observed in the course of patient administration in the ICU correlated with the clinical condition and the course of disease for every observed patient.

\* \* \*

Some embodiments of the invention include a kit including materials for performing the various steps of the invention. In one exemplary embodiment of a kit for detecting toxemia in a subject patient from a sample of the subject patient's blood serum containing carrier proteins, the kit includes an amount of labeled probe and an amount of solvent. The amounts of probe and solvent are such that when mixed with aliquot of serum having about a predetermined volume (e.g., 50, 60, 70, 80, 90, 100, or more µL), the mixture will achieve the results described above, and/or have the proportions of ingredients described above.

In other embodiments, the kit can include components for performing the various steps and/or portions of the present methods, as described herein. In some embodiments, the kit can further include instructions for performing the various steps or portions of the present methods, as described above.

In any of the various embodiments described or suggested in this disclosure, the methods can comprise or be limited to any combination of the steps and/or features characteristics described, unless the context explicitly or necessarily precludes the combination. For example, one embodiment of the present method can include mixing probe with an aliquot and measuring the concentrations of bound and unbound probe; and another embodiment can include mixing probe and solvent with the aliquot, measuring the concentrations of bound and unbound probe, and normalizing the concentrations to substantially negate the changes in concentrations caused by the added. By way of another example, one embodiment of the present kits can include a pipette and an amount of probe; another embodiment can include an amount of probe and an amount of solvent; and another embodiment can include an amount of probe, an amount of liquid solution, and an amount of solvent.

The various illustrative embodiments of methods and kits described herein are not intended to be limited to the particular forms disclosed. Rather, they include all modifications, equivalents, and alternatives falling within the scope of the claims. For example, embodiments of the present methods can include measuring (indirectly) the concentrations of bound and unbound probe in a mixture (aliquot, probe, solvent) with EPR spectroscopy, fluorescent spectroscopy, or other suitable methods described or otherwise known or developed in the art.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A method for detecting toxemia in a subject patient, comprising the steps of:
    mixing a labeled hydrophobic probe capable of binding to carrier proteins with an aliquot of a subject patient's extracellular fluid containing carrier proteins, the amount of probe such that the molar ratio of the probe to the carrier proteins is between about 0.3 and about 1.5;
    mixing a solvent with the aliquot, the solvent such that when added to the aliquot and probe the solubility of the probe is increased in the aliquot, and the amount of solvent sufficient to dissociate a portion of the probe from the carrier proteins without causing significant dissociation of toxins from the carrier proteins;
    analyzing the mixture comprising the aliquot, probe, and solvent to determine the binding efficiency of the carrier proteins; and
    comparing the subject binding efficiency to at least one control binding efficiency for at least one non-toxemic control patient.

2. The method of claim 1, where the step of analyzing the mixture comprises:
    measuring the concentrations of protein-bound and unbound probe in the mixture; and
    deriving a subject binding efficiency of the carrier proteins from at least the concentrations of the protein-bound and unbound probe.

3. The method of claim 1, where the probe and the solvent are mixed with one another prior to either being mixed with the aliquot.

4. The method of claim 1, where the probe comprises at least one of: an organic molecule having between 8 and 28 Carbon atoms, a fatty acid, a long-chain fatty acid, 16-DOXYL-stearic acid, and lysophospholipid.

5. The method of claim 1, where the solvent comprises two or more substances.

6. The method of claim 1, where the amount of solvent mixed with the aliquot and the probe is such that the solvent does not induce significant conformational changes to the carrier proteins.

7. The method of claim 1, where the amount of solvent mixed with the aliquot and the probe is sufficient to increase the concentration of unbound probe in the mixture of the aliquot, the probe, and the solvent to at least 5 times greater than the concentration of unbound probe in a mixture of the aliquot and the probe without the solvent.

8. The method of claim 1, where the solvent is alcohol.

9. The method of claim 1, where the volume of the amount of the solvent mixed with the aliquot is less than about 30% of the volume of the aliquot.

10. The method of claim 9, where the volume of the amount of the solvent mixed with the aliquot is less than about 10% of the volume of the aliquot.

11. The method of claim 1, further comprising the step of:
    normalizing the subject binding efficiency to account for the reduction in carrier-protein concentration caused by the amount of solvent in the mixture.

12. The method of claim 11, where the steps of deriving the subject binding efficiency and normalizing the subject binding efficiency are performed simultaneously.

13. The method of claim 11, further comprising the step of:
    normalizing the subject binding efficiency to account for the reduction in carrier-protein concentration caused by medical conditions of the patient.

14. The method of claim 1, where the at least one control binding efficiency comprises a range of control binding efficiencies.

15. The method of claim 1, further comprising repeating the steps of mixing a probe, mixing a solvent, measuring the concentrations, deriving a subject binding efficiency, for each of two or more aliquots, and where a different amount of solvent is used for each of the two or more repetitions.

16. The method of claim 15, where the subject binding efficiencies derived for the two or more repetitions are averaged to derive an average subject binding efficiency, and where the average subject binding efficiency is compared in the step of comparing the subject binding efficiency to at least one control binding efficiency.

17. The method of claim 1, where the volume of the aliquot is less than about 100 µL.

18. The method of any of claim 1, further comprising the step of:
    diagnosing, responsive to the subject binding efficiency being less than the at least one control binding efficiency, the subject patient with toxemia.

19. The method of claim 1, where the probe is labeled with at least one of: a spin-label, a radioactive label, and a fluorescent label.

20. The method of claim 1, where the extracellular fluid includes at least one of: blood serum, blood plasma, lymph fluid, and spinal fluid.

21. A method for detecting toxemia in a subject patient, comprising the steps of:
    mixing a labeled hydrophobic probe capable of binding to carrier proteins with an aliquot of a subject patient's extracellular fluid containing carrier proteins, the amount of probe such that the molar ratio of the probe to the carrier proteins is between about 0.3 and about 1.5;
    mixing a solvent with the aliquot, the solvent such that when added to the aliquot and probe the solubility of the probe is increased in the aliquot, and the amount of solvent sufficient to dissociate a portion of the probe from the carrier proteins without causing significant dissociation of toxins from the carrier proteins;

analyzing the mixture comprising the aliquot, the probe, and the solvent to determine a subject toxin-evacuation parameter of the carrier; and comparing the subject toxin-evacuation parameter to at least one control toxin-evacuation parameter for a non-toxemic control patient.

22. The method of claim 21, where the step of analyzing the mixture comprises:

measuring the concentrations of protein-bound and unbound probe in the mixture;

deriving a subject binding efficiency of the carrier proteins from at least the concentrations of the protein-bound and unbound probe;

deriving a subject toxin-evacuation parameter of the carrier proteins as the square of the subject binding efficiency.

23. A kit for detecting toxemia in a subject patient from a sample of the subject patient's extracellular fluid containing carrier proteins, comprising:

a labeled hydrophobic probe capable of binding to carrier proteins, the amount of probe such that when mixed with an aliquot having a predetermined volume of the extracellular fluid the molar ratio of the probe to the carrier proteins is in the range of about 0.3 to about 1.5; and a solvent, the solvent such that when mixed with the probe and the aliquot the solubility of the probe is increased in the aliquot, and the amount of solvent sufficient to dissociate a portion of the probe from the carrier proteins without causing significant dissociation of toxins from the carrier proteins.

24. The kit of claim 23, further comprising:

instructions for:

mixing a labeled hydrophobic probe capable of binding to carrier proteins with an aliquot having a predetermined volume of a subject patient's extracellular fluid containing carrier proteins, the amount of probe such that the molar ratio of the probe to the carrier proteins is between about 0.3 to about 1.5; and mixing an amount of solvent with the mixture of the probe and the aliquot sufficient to dissociate a portion of the probe from the carrier proteins without causing significant dissociation of toxins from the carrier proteins.

25. The kit of claim 24, further comprising:

instructions for:

analyzing the mixture of the aliquot, the probe, and the solvent to determine the subject binding efficiency of the carrier proteins; and comparing the subject binding efficiency to at least one control binding efficiency for a non-toxemic control patient.

26. The kit of claim 25, wherein the instructions for analyzing the mixture comprise instructions for:

measuring the concentrations of protein-bound and unbound probe in the mixture; and driving a subject binding efficiency of the carrier proteins from at least the concentrations of the protein-bound and unbound probe.

\* \* \* \* \*